United States Patent [19]

Krause et al.

[11] Patent Number: 4,987,010
[45] Date of Patent: Jan. 22, 1991

[54] METHOD FOR MANUFACTURING A FILM RESISTOR

[75] Inventors: Hans Krause, Ban Nauheim; Helmut Stoll, Liederbach, both of Fed. Rep. of Germany

[73] Assignee: Leybold AG, Fed. Rep. of Germany

[21] Appl. No.: 411,736

[22] Filed: Sep. 25, 1989

[30] Foreign Application Priority Data

Mar. 1, 1989 [DE] Fed. Rep. of Germany ....... 3906405

[51] Int. Cl.$^5$ ............................................. B05D 5/12
[52] U.S. Cl. ..................................... 427/103; 427/39; 427/99; 156/643
[58] Field of Search .......................... 427/103, 99, 39; 156/643

[56] References Cited

U.S. PATENT DOCUMENTS

| | | | |
|---|---|---|---|
| 4,288,776 | 9/1981 | Holmes | 427/103 |
| 4,585,517 | 4/1980 | Stemple | 156/643 |
| 4,822,697 | 4/1989 | Haluska et al. | 427/99 |
| 4,895,734 | 1/1990 | Yoshida et al. | 427/99 |

*Primary Examiner*—Stanley Silverman
*Attorney, Agent, or Firm*—Hill, Van Santen, Steadman & Simpson

[57] ABSTRACT

A method for manufacturing a film resistor for use as a thermal conductivity detector, particularly for gas analyzers. The film resistor is composed of a carrier of insulating material and of a thin resistance layer, preferably composed of platinum, that is applied to the carrier by cathode sputtering in an atmosphere inert gas. The resistant layer and the carrier are cleaned proceeding from the metallized side using an argon sputtering process. The film resistor is then coated with at least one plasma-enhanced CVD layer for the purpose of protection against aggressive gases.

17 Claims, 1 Drawing Sheet

METHOD FOR MANUFACTURING A FILM RESISTOR

BACKGROUND OF THE INVENTION

1. Field of the Invention

The present invention is directed to a method for manufacturing a film resistor to be used as a thermal conductivity detector, particularly in gas analyzers.

2. Description of the Prior Art

It is known in the art to use precision resistors as resistance thermometers. In such devices, a thin platinum layer is applied onto an electrically non-conductive carrier, such as glass or ceramic. The thin platinum layer may be applied by employing a high-vacuum evaporation or cathode sputtering method, whereby the layer may cover the entire surface of the carrier or may cover only a partial region thereof. This is disclosed in German Patent DE-PS No. 828930.

It is likewise known in the art, as shown in German published application DE-OS No. 2507731, to employ precision platinum resistors composed of an insulating carrier formed from a material having a greater coefficient of thermal expansion than platinum at temperatures between 0° and 1000° C. Such precision resistors, however, are restricted with respect to the types of materials which may be utilized as the carrier.

Thin-film resistors, in contrast to the precision resistors used in resistance thermometers, are constructed having extremely high resistance values and optimally low temperature coefficients. In the manufacture of such thin-film resistors, it is known, as disclosed in German published application DE-OS No. 2019091, to apply the resistance layers by cathode sputtering in an argon-atmosphere for the embedding of foreign atoms.

A method for manufacturing a precision film resistor for use in resistance thermometers is also disclosed in German patent DE-PS 2558752. The precision film resistor disclosed therein is composed of an insulating carrier and a thin resistance layer of platinum which is disposed on the carrier by cathode sputtering in an atmosphere containing an inert gas. The following steps are suggested:

(a) employment of a krypton-oxygen mixture or xenon-oxygen mixture to produce an inert gas atmosphere;
(b) application of a countervoltage to the carrier;
(c) post-tempering the sputtered-on resistant layer in an oxidizing atmosphere at a temperature between 700° and 1200° C.

None of the above-noted precision resistors are suitable for integration in gas analyzers which are utilized, for example, in analyzing the exhaust gas during the development of reciprocating motors by the automobile industry. Such exhaust gases are extremely reactive and readily penetrate the known protective layers. Consequently, after such precision resistors are exposed to such gasses for a relatively short duration, the resistance layer is destroyed.

It is therefore an object of the invention to set forth a method for manufacturing a precision film resistor suitable for high operating temperatures (i.e., exhibit a high intrinsic temperature stability, particularly at temperatures above 150° C.), which is insensitive to aggressive gases and which can be manufactured in a particularly economical manner.

SUMMARY OF THE INVENTION

The present invention is directed to a method for fabricating a film resistor which is insensitive to aggressive gases. First, a resistance layer is disposed on the carrier. The resistance layer and the carrier are then cleaned, proceeding from the metallized side, with an argon sputtering process. The layer and carrier are then coated with at least one plasma-enhanced chemical vapor deposition (CVD) layer for the purpose of protection, particularly against aggressive gases. The protective layer is optimally fashioned as a hard layer of $SiO_2$, SiC, SiC/SiN or SiC/c.

BRIEF DESCRIPTION OF THE DRAWINGS

Other objects, features and advantages of the invention will be best understood from the following detailed description taken in accompaniment with the associated figures, of which.

DESCRIPTION OF THE PREFERRED EMBODIMENTS

Figure 1:
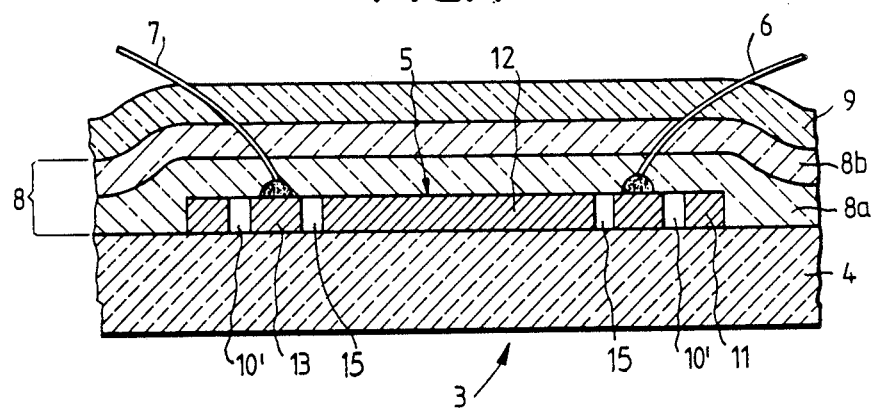
FIG. 1 is a cross-sectional view of a thermal conductivity detector constructed in accordance with the inventive method.
Figure 2:
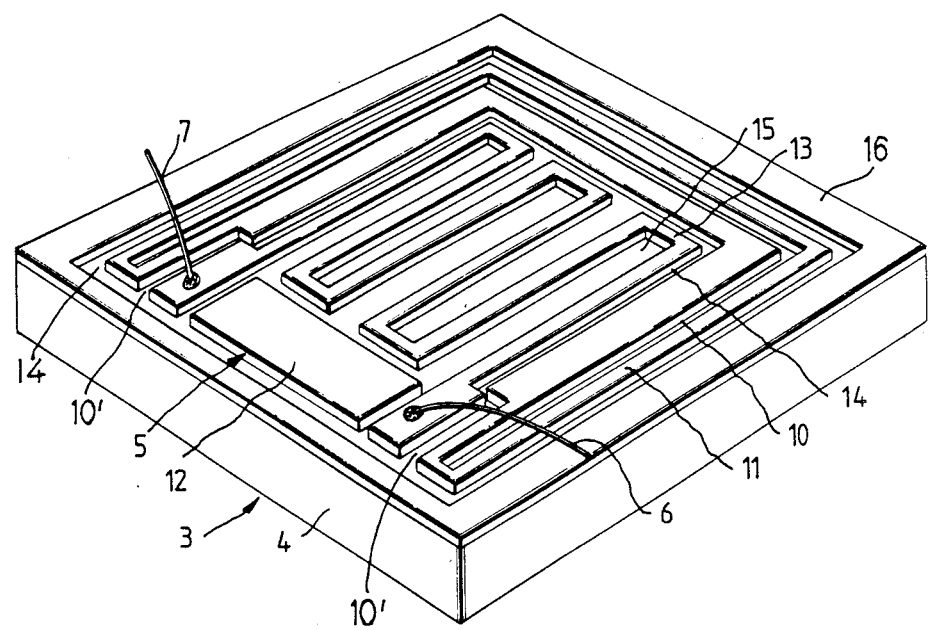
FIG. 2 is a perspective view of a thermal conductivity detector without the protective layers disposed thereon.

A thermal conductivity detector 3 is shown which comprises an insulating carrier 4 on which a resistance layer 5 of platinum is applied by cathode sputtering. This platinum resistance layer 5 is permeated by incisions, recesses or groves 10, 14, 15 so that a centralized, meander-shaped section 13 and two edge sections 11, 12 that surround or enclose section 13 are formed. The actual precision resistor is formed by the meander-shaped section 13 whose two arm-shaped extensions are soldered to the power leads 6, 7.

After the resistance layer 5 is applied and after the power leads 6, 7 are attached, the metallized side is cleaned using an argon sputtering process. A first protective layer 8a of $SiO_2$ is then applied followed by a second protective layer 8b of SiC or SiN. Together, layers 8a and 8b form a protective layer package 8. A third layer 9 of SiC is also applied to further protect the device. All of the layers 8a, 8b, 9 are applied using a plasma-enhanced CVD method.

Alternatively, the protective layer package 8 may be formed of a first, non-excessively thin $SiO_2$ layer having poor thermal conductivity and of a second, thinner SiC or SiN layer having good thermal conductivity. The protective layer package 8 may ultimately be applied n subsequent times. The thickness ratio of the $SiO_2$ to the SiC protective layer dictates a parameter determinative of the thermal resistance of the layer and the heat flow in lateral and transverse directions. Thus, the layer thickness ratio can be utilized for optimizing the thermal conductivity detector response with respect to high signal values or very short response times.

At least one part of the resistance layer comprises a meander-like configuration and is divided from edge sections 11, 12 by trenches, grooves or incisions 10' which are incised through the resistance layer 5 to the carrier 4. The incisions or grooves 10' form a heat elimination barrier that prevents a rapid temperature exchange from occurring between the central section 13 and the radially outside sections 11, 12.

In order to make any heat exchange between the resistance layer 5 and the ambient atmosphere more difficult, the edge section 11 of the resistance layer 5 surrounding the meander-shaped part are separated from the exterior edge section 16 of the device by recesses 14 incised down to the carrier 4. Furthermore, a groove 10 is incised in the interior region of the edge section 11. Optimally, the recesses, grooves, or incisions proceed parallel to one another.

Although other modifications and changes may be suggested by those skilled in the art, it is the intention of the inventor to embody within the patent warranted hereon any changes and modifications as reasonably and properly come within the scope of this contribution to the art.

We claim:

1. A method for fabricating a film resistor comprising the steps of:
    depositing a resistance layer on a surface of an insulating carrier;
    cleaning said resistance layer and said surface of said insulating carrier using an argon sputtering process;
    depositing a plasma-enhanced CVD protective layer on said resistance layer and said surface of said insulating carrier.

2. A method for fabricating a film resistor as recited in claim 1, wherein the step of depositing a plasma-enhanced CVD protective layer is further defined by depositing at least one plasma-enhanced CVD protective layer selected from the group consisting of $SiO_2$, SiC, SiC/SiN or SiC/C.

3. A method for fabricating a film resistor as recited in claim 1, wherein the step of depositing a plasma-enhanced CVD protective layer is further defined by depositing a $SiO_2$ plasma-enhanced CVD protective layer.

4. A method for fabricating a film resistor as recited in claim 3, further comprising the steps of:
    depositing a further plasma-enhanced CVD protective layer on said $SiO_2$ layer, said further protective layer formed from a material selected from the group consisting of SiC or SiN, said plasma enhanced CVD protective layer and said further plasma-enhanced CVD protective layer forming a protective layer package; and
    depositing a still further plasma-enhanced CVD protective layer on said further protective layer, said still further protective layer formed as a SiC layer.

5. A method for fabricating a film resistor as recited in claim 4, further comprising the step of applying a plurality of successive protective layer packages before depositing said still further plasma enhanced CVD protective layer.

6. A method for fabricating a film resistor as recited in claim 4, further comprising the step of adjusting the thickness ratio between said plasma-enhanced CVD protective layer and said further plasma-enhanced CVD protective layer to control the thermal conductivity of said protective layer package.

7. A method for fabricating a film resistor as recited in claim 1, further comprising the steps of:
    forming a meander-like configuration in said resistance layer; and
    incising a peripheral groove about said meander-like configuration to divide said meander-like configuration from a remaining portion of said resistance layer.

8. A method for fabricating a film resistor as recited in claim 7, further comprising the step of incising a groove in said remaining portion of said resistance layer thereby to form an edge section, said edge section disposed between said meanderlike configuration and a still further remaining portion of said resistance layer.

9. A method for fabricating a film resistor as recited in claim 8, further comprising the step of incising an interior groove in said edge section.

10. A method for fabricating a film resistor comprising the steps of:
    depositing a resistance layer on a surface of an insulating carrier;
    cleaning said resistance layer and said surface of said insulating carrier using an argon sputtering process;
    depositing a plasma-enhanced CVD protective layer on said resistance layer and said surface of said insulating carrier;
    depositing a further plasma-enhanced CVD protective layer, said plasma-enhanced CVD protective layer and said further plasma-enhanced CVD protective layer forming a protective layer package; and
    adjusting the thickness ratio between said plasma-enhanced CVD protective layer and said further plasma-enhanced CVD protective layer to control thermal conductivity of said protective layer package.

11. A method for fabricating a film resistor as recited in claim 10, further comprising the steps of:
    forming a meander-like configuration in said resistance layer; and
    incising a peripheral groove about said meander-like configuration to divide said meander-like configuration from a remaining portion of said resistance layer.

12. A method for fabricating a film resistor as recited in claim 11, further comprising the step of incising a groove in said remaining portion of said resistance layer thereby to form an edge section, said edge section disposed between said meander-like configuration and a still further remaining portion of said resistance layer.

13. A method for fabricating a film resistor as recited in claim 13, further comprising the step of incising an interior groove in said edge section.

14. A method for fabricating a film resistor comprising the steps of:
    depositing a resistance layer on a surface of an insulating carrier;
    cleaning said resistance layer and said surface of said insulating carrier using an argon sputtering process;
    depositing a plasma-enhanced CVD $SiO_2$ protective layer on said resistance layer and said surface of said insulating carrier;
    depositing a further plasma-enhanced CVD protective layer on said plasma-enhanced CVD $SiO_2$ protective layer, said further protective layer formed from a material selected from the group consisting of SiC or SiN, said plasma-enhanced CVD $SiO_2$ protective layer and said further plasma-enhanced CVD protective layer forming a protective layer package; and
    depositing a still further plasma-enhanced CVD protective layer on said further protective layer, said still further plasma-enhanced CVD protective layer formed as a SiC layer.

15. A method for fabricating a film resistor as recited in claim 14, further comprising the steps of:
- forming a meander-like configuration in said resistance layer; and
- incising a peripheral groove about said meander-like configuration to divide said meander-like configuration from a remaining portion of said resistance layer.

16. A method for fabricating a film resistor as recited in claim 15, further comprising the step of incising a groove in said remaining portion of said resistance layer thereby to form an edge section, said edge section disposed between said meander-like configuration and a still further remaining portion of said resistance layer.

17. A method for fabricating a film resistor as recited in claim 16, further comprising the step of incising an interior groove in said edge section.

* * * * *